United States Patent
Maron et al.

(10) Patent No.: US 11,039,993 B2
(45) Date of Patent: Jun. 22, 2021

(54) COMPOSITIONS WITH NATURAL OILS FOR PROVIDING A PROTECTIVE BARRIER

(71) Applicant: L'OREAL, Paris (FR)

(72) Inventors: Zachary Maron, Jersey City, NJ (US); Paul Pierre Bonvallet, Westfield, NJ (US); Susan Halpern Chirch, Basking Ridge, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/141,599

(22) Filed: Sep. 25, 2018

(65) Prior Publication Data

US 2020/0093721 A1    Mar. 26, 2020

(51) Int. Cl.
| | | |
|---|---|---|
| *A61K 8/37* | (2006.01) | |
| *A61Q 5/00* | (2006.01) | |
| *A61K 8/34* | (2006.01) | |
| *A61K 8/92* | (2006.01) | |
| *A61K 8/9789* | (2017.01) | |
| *A61K 8/33* | (2006.01) | |
| *A61K 8/67* | (2006.01) | |
| *A61K 8/42* | (2006.01) | |
| *A61K 8/55* | (2006.01) | |
| *A61K 8/891* | (2006.01) | |
| *A61K 8/49* | (2006.01) | |
| *A61K 8/96* | (2006.01) | |
| *A61Q 19/00* | (2006.01) | |

(52) U.S. Cl.
CPC ................ *A61K 8/37* (2013.01); *A61K 8/33* (2013.01); *A61K 8/345* (2013.01); *A61K 8/375* (2013.01); *A61K 8/42* (2013.01); *A61K 8/4946* (2013.01); *A61K 8/55* (2013.01); *A61K 8/678* (2013.01); *A61K 8/891* (2013.01); *A61K 8/922* (2013.01); *A61K 8/965* (2013.01); *A61K 8/9789* (2017.08); *A61Q 5/00* (2013.01); *A61Q 19/00* (2013.01); *A61K 2800/30* (2013.01); *A61K 2800/31* (2013.01)

(58) Field of Classification Search
CPC .......... A61K 8/37; A61K 8/9789; A61K 8/33; A61K 8/345; A61K 8/375; A61K 8/42; A61K 8/4946; A61K 8/55; A61K 8/678; A61K 8/891; A61K 8/922; A61K 8/965; A61K 2800/30; A61K 2800/31; A61Q 5/00; A61Q 19/00
See application file for complete search history.

(56) References Cited

U.S. PATENT DOCUMENTS

| | | |
|---|---|---|
| 5,160,738 A | 11/1992 | MacAulay et al. |
| 6,503,944 B1 | 1/2003 | Chanchani |
| 7,195,787 B1 | 3/2007 | Pykett et al. |
| 8,512,683 B2 | 8/2013 | SaNogueira et al. |
| 2010/0074965 A1 | 3/2010 | Erisson nee Conry et al. |
| 2017/0143616 A1* | 5/2017 | Page ........................ A61K 8/25 |

OTHER PUBLICATIONS

U.S. Appl. No. 16/141,665, filed Sep. 25, 2018, Zachary Moran.
Dans Mintel, Hydrogenated Vegetable Oil et Tribehenin et Glyceryl Stearate et Glyceryl Behenate NOT Aqua et soins de la peau = 1 produit (Exozen-Hydrating Face Mask), Jul. 2012.

* cited by examiner

*Primary Examiner* — Celeste A Roney
(74) *Attorney, Agent, or Firm* — McNees Wallace & Nurick LLC

(57) ABSTRACT

A composition provides a protective barrier and includes glyceryl dibehenate, tribehenin, and glyceryl behenate, a surfactant that includes glyceryl stearate, hydrogenated vegetable oil, one or more additional fatty compounds, and one or more triglyceride. The composition optionally includes wax, a hydrating agent, and may be essentially free of or is devoid of one or more of petrolatum, mineral oil and water. The composition provides occlusivity and hydration effects that are comparable to compositions that include one or more of petrolatum, mineral oil and lanolin.

36 Claims, 1 Drawing Sheet

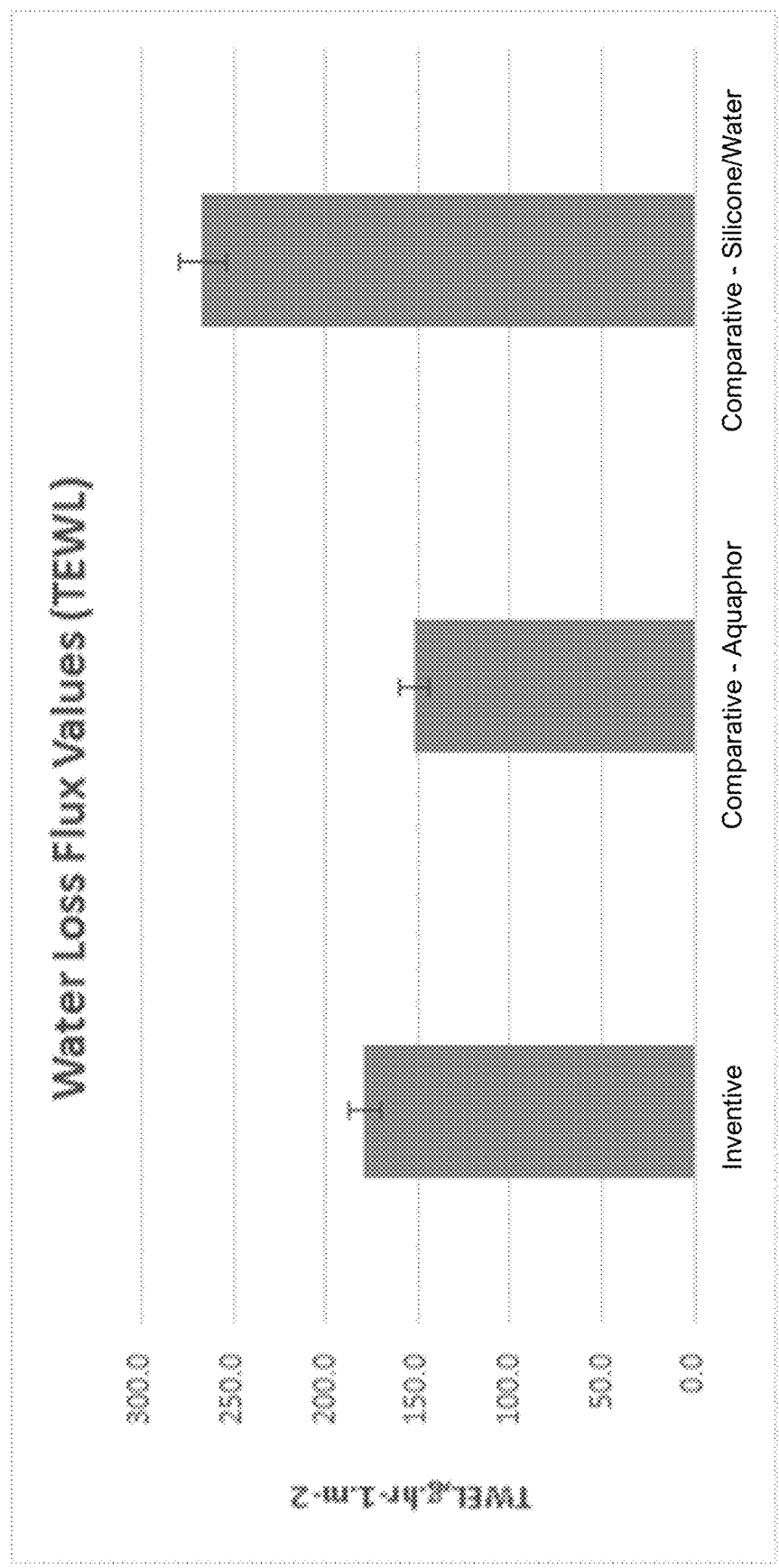

COMPOSITIONS WITH NATURAL OILS FOR PROVIDING A PROTECTIVE BARRIER

FIELD OF THE INVENTION

The invention relates to protective barrier compositions that provide a protective occlusive barrier when applied to keratinous substrates, for example, human skin and human hair.

BACKGROUND OF THE INVENTION

Topical formulations for keratinous substrates, for example skin, can include occlusive ingredients. The occlusive ingredients provide a barrier that protects against water loss and incursion of irritants and contaminants. Well known occlusive ingredients include hydrocarbons, for example in the form of petrolatum (petroleum jelly), and mineral oils, each of which have been included in a wide variety of skin and hair products. Such products are known for their spreadable texture and shapability, and their effectiveness in preventing water loss and preserving hydration of skin and hair. Despite these beneficial features, petrolatum, mineral oil and lanolin can have unpleasant tactile and aesthetic properties, including one or more of waxiness, stickiness and warming sensation. And these materials can present health and environmental concerns.

There is a need for a composition that overcomes one or more of the aforementioned drawbacks associated with products that employ one or more of petrolatum, mineral oil and lanolin. Such a composition would provide one or more of good spreadability, pleasant tactile and aesthetic properties, and a protective barrier that preserves hydration, for example in the skin and hair, in a manner that is at least comparable to that of petrolatum and mineral containing products.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

The protective barrier composition and methods of making them are characterized, in various embodiments, as comprising an emollient blend comprising glyceryl dibehenate, tribehenin and glyceryl behenate; a surfactant comprising glyceryl stearate; hydrogenated vegetable oil; one or more additional oils selected from fatty plant derived oils and synthetic oils, the fatty plant derived oils and synthetic oils comprising one or more fatty chains having a chain length from and including C8 to C24; one or more triglycerides; and optionally one or more wax. The emollient blend, the surfactant, and the hydrogenated vegetable oil are present, by weight, at a ratio of from about 2:2:1 to about 4:4:1, based on the weight of the protective barrier composition. In one example, the emollient blend, the surfactant, and the hydrogenated vegetable oil are present, by weight, at a ratio of about 2:2:1. In another example, the emollient blend, the surfactant, and the hydrogenated vegetable oil are present, by weight, at a ratio of about 3:3:1, and in yet another example the emollient blend, the surfactant, and the hydrogenated vegetable oil are present, by weight, at a ratio of about 4:4:1.

In some embodiments, the emollient blend comprises glyceryl dibehenate, tribehenin and glyceryl behenate present, by weight, at a ratio of about 1:1:1, based on the weight of the emollient blend.

In some embodiments each of the emollient blend and the surfactant, is present in the composition at a concentration, by weight, in the range from about 2% to about 20%, based on the total weight of the protective barrier composition, and wherein the combination of the emollient blend and the surfactant is present in the composition at a concentration, by weight, of up to and including about 30%, based on the total weight of the protective barrier composition.

In some embodiments, the hydrogenated vegetable oil, the one or more additional oils selected from fatty plant derived oils and synthetic oils, and the one or more triglycerides, in combination, are present in the composition at a concentration, by weight, in the range from about 50% to about 80%, based on the total weight of the protective barrier composition.

In some embodiments, the emollient blend and the surfactant comprising glyceryl stearate are present at a ratio of 1:1, by weight, based on the weight of the protective barrier composition.

The one or more triglyceride may comprise one or more triglycerides, the one or combination thereof present in the composition at a concentration, by weight, of between about 2% to about 50%, based on the total weight of the protective barrier composition. In some embodiments, the one or more triglycerides is selected from caprylic/capric triglyceride, triglycerides having a chain length from and including C10 to C18, and combinations thereof.

In accordance with the various embodiments, the protective barrier composition comprises one or more compounds selected from hydrating agents and solvents, and may further comprise any one or more, each, of actives, chelating agents, silicone oils, clays, conditioning agents, and combinations thereof, together with other suitable additives.

In some embodiments, the protective barrier composition is essentially free or devoid of one or more of petrolatum, mineral oil, lanolin and water. In some particular embodiments, the protective barrier composition is devoid of one or more of petrolatum, mineral oil, lanolin and water. In some particular embodiments, the protective barrier composition is devoid of petrolatum, mineral oil, lanolin and water. In some embodiments, the protective barrier composition is essentially devoid of water other than trace amounts (i.e., present at a concentration that does not exceed 5% by weight, and more preferably not more than 1% by weight, based on the weight of the composition). And in some embodiments, the protective barrier composition is essentially free or devoid of preservatives.

In accordance with the various embodiments, the composition provides a protective occlusive barrier to keratinous tissue. In some examples, the composition that lacks one or more of petrolatum, mineral oil and lanolin exhibits physical properties including viscosity, spreadability, rheology that is comparable to products containing one or more of petrolatum, mineral oil and lanolin.

Other features and advantages of the present invention will be apparent from the following more detailed description, by way of example, the principles of the invention.

This disclosure describes particular embodiments in accordance with the general inventive concepts and is not intended to limit the scope of the invention in any way. Indeed, the invention as described in the specification is broader than and unlimited by the particular embodiments set forth herein, and the terms used herein have their full ordinary meaning.

BRIEF DESCRIPTION OF THE DRAWINGS

Features and advantages of the general inventive concepts will become apparent from the following description made with reference to the accompanying drawings, including drawings represented herein, of which the following is a brief description:

FIG. 1 shows water loss results (TEWL) with compositions according to the instant disclosure and comparative formulations.

DETAILED DESCRIPTION OF THE INVENTION

The term "occlusive barrier" as used herein means and refers to a composition that includes agents that form an occlusive barrier that minimizes or prevents water loss from skin.

The term "anhydrous" as used herein means that a composition is anhydrous in that water has not been added as a component. In some embodiments, a composition is devoid of water. Those of skill in the art will appreciate that water may be present in a composition via one or more of its presence in the formulation components, processing conditions and absorption from the atmosphere; thus, in some embodiments a composition may be "essentially anhydrous" wherein water is present at a concentration that does not exceed 5% by weight, and more preferably not more than 1% by weight, based on the weight of the composition.

The terms "petrolatum-free" and "mineral oil-free" as used herein mean that a composition lacks one or more of petrolatum, mineral oil and lanolin. Those of skill in the art will appreciate that one or more of petrolatum, mineral oil and lanolin may be present in a composition via one or more of its presence in the formulation components and processing condition. Accordingly, in some embodiments, a composition may be "essentially free" from one or more of petrolatum, mineral oil and lanolin, wherein one or more of petrolatum, mineral oil and lanolin is present at a concentration that does not exceed 5% by weight, and more preferably not more than 1% by weight, based on the weight of the composition. In some embodiments, one or more of petrolatum, mineral oil and lanolin has not been added as a component in the composition. In some embodiments, a composition is devoid of one or more of petrolatum, mineral oil and lanolin.

The term "plant derived oils" as used herein means fatty plant derived oils that contain one or more fatty chain, and in some embodiments the fatty chain has a chain length from and including C8 to C24. Thus, in some embodiments, a fatty derived plant oil may comprise one or a blend of oils having a chain length of C8, C9, C10, C11, C12, C13, C14, C15, C16, C17, C18, C19, C20, C21, C22, C23, and C24.

The term "triglycerides" as used herein means one or more of caprylic/capric triglyceride, and triglycerides having a chain length from and including C10 to C18. Thus, in some embodiments, triglycerides may comprise one or a blend of triglycerides having a chain length of C10, C11, C12, C13, C14, C15, C16, C17, and C18.

According to the disclosure, an composition is provided for providing a protective barrier, the composition comprising an emollient blend that includes glyceryl dibehenate, tribehenin and glyceryl behenate, a surfactant that includes glyceryl stearate, and one or more fatty compounds that include one or more fatty plant derived oil or synthetic oil that comprises one or more fatty chain having a chain length from and including C8 to C24. In some embodiments, the composition comprises one or more triglyceride. In some embodiments, the compositions comprise one or more of hydrating agents, solvents, actives, vitamins, chelating agents. In some embodiments, the protective barrier composition is essentially free of or is devoid of one or more of petrolatum, mineral oil and lanolin. In some embodiments, the protective barrier composition is essentially free of or is devoid of water.

The composition provides occlusivity when applied to skin to help maintain a favorable environment maintenance of skin hydration, and for skin healing. In some particular embodiments, the composition is free of petrolatum, mineral oil and lanolin. The composition provides the surprising and unexpected benefits of a unique texture that mimics the thickness and spreadability of hydrocarbon and mineral oil-based occlusive barrier products. Also, surprisingly, the occlusivity and hydration effects of the composition are comparable to compositions that include one or more of petrolatum, mineral oil and lanolin.

Emollient Blend

In accordance with the disclosure, provided are compositions that comprise an emollient blend comprising glyceryl dibehenate, tribehenin and glyceryl behenate. In accordance with the various embodiments, the emollient blend comprises the raw materials comprising glyceryl dibehenate, tribehenin and glyceryl behenate, each, alone or as blended, may be provided in a solvent.

In accordance with the various embodiments, each of the emollient blend components glyceryl dibehenate, tribehenin and glyceryl behenate may be present in a composition in a ratio of from about 1:1 to about 2:1, by weight, based on the weight of the emollient blend. Thus, in some embodiments, the emollient blend comprises glyceryl dibehenate, tribehenin and glyceryl behenate present, at a ratio of about 1:1:1, by weight, based on the weight of the emollient blend.

As used herein, glyceryl dibehenate is used to refer to the compound that is alternately identified in the art as 2-Hydroxypropane-1,3-diyl didocosanoate; Docosanoic acid, 1,1'-(2-hydroxy-1,3-propanediyl) ester; 1,3-dibehenin; 1-Behenoyl-3-behenoyl-sn-glycerol; 1,2,3-Propanetriol 1,3-dibehenate; 1-Docosanoyl-3-docosanoyl-sn-glycerol; and Diacylglycerol(22:0/0:0/22:0). As used herein, Tribehenin is used to refer to the compound that is alternately identified in the art as 2,3-propanetriyl ester behenic acid; 1,2,3-propanetriyl ester docosanoic acid; 1,2,3-propenetriol tridocosanoate; behenic acid, 1,2,3-propanetriyl ester; docosanoic acid, 1,2,3-propanetriyl ester; docosanoic acid, 1,2,3propanetriyl ester; glyceryl tribehenate; propane-1,2,3-triyl tridocosanoate; compritol 888; and docosanoin, tri-(7ci,8ci). And, as used herein, glyceryl behenate is used to refer to the compound that is alternately identified in the art as 2,3-dihydroxypropyl docosanoate; 2,3-dihydroxypropyl ester docosanoic acid; behenic acid monoglyceride; docodanoin, mono-; docosanoic acid, 2,3-dihydroxypropyl ester; docosanoic acid, monoester with 1,2,3-propanetriol; glycerin monobehenate; glycerol monobhenate; glyceryl monobehenate; mono-docodanoin; and monoester with 1,2,3-propanetriol docosanoic acid.

Surfactant

In accordance with the various embodiments, the emollient blend is present in the composition together with one or more surfactant comprising glyceryl stearate, the combination being present in the composition at a concentration up to and including about 30% by weight, based on the weight of the protective barrier composition. In some embodiments, the combination is present in the range from about 1% to about 30%, or from about 1% to about 25%, or from about 1% to about 10%, or from about 1% to about 7%, or from about 2% to about 6%, or from about 3% to about 5%, or from about 5% to about 15%, or from about 6% to about 10%, or any suitable combination, sub-combination, range, or sub-range thereof by weight, based on the weight of the composition.

In accordance with the various embodiments, the surfactant may be present in the composition in a ratio of the surfactant to emollient blend of from about 2:1 to about 1:2, by weight, based on the weight of the protective barrier composition. Thus, in some embodiments, the one or more surfactant comprising glyceryl stearate and the emollient blend may be present at a ratio of 1:1, by weight, based on the weight of the protective barrier composition.

In accordance with the various embodiments, the emollient blend is present in the composition at a concentration, by weight, of at least about 2%, based on the total weight of the protective barrier composition.

In accordance with the various embodiments, the emollient blend is present in the composition at a concentration, by weight, based on the total weight of the protective barrier composition, in the range from about 0.01% to about 20%, or from about 2% to about 20%, or from about 0.05% to about 10%, or from about 0.1% to about 4%, or from about 0.1% to about 3.5%, or from about 0.7% to about 1.5%, or from about 3.5% to about 5%, or any suitable combination, sub-combination, range, or sub-range thereof by weight, based on the weight of the composition.

Thus, the emollient blend is present, by weight, based on the total weight of the composition, each one or the combination present from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 to about 20 weight percent, including increments and ranges therein and there between.

More particularly, each one of glyceryl dibehenate, tribehenin and glyceryl behenate is present in the composition at a concentration, by weight, based on the total eight of the protective barrier composition, in the range from about 0.01% to about 20%, or from about 2% to about 20%, or from about 0.05% to about 10%, or from about 0.1% to about 4%, or from about 0.1% to about 3.5%, or from about 0.7% to about 1.5%, or from about 3.5% to about 5%, or any suitable combination, sub-combination, range, or sub-range thereof, by weight, based on the weight of the composition.

Thus, each one of glyceryl dibehenate, tribehenin and glyceryl behenate is present, by weight, based on the total weight, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 to about 20 weight percent, including increments and ranges therein and there between.

The composition comprises the emollient blend together with a surfactant and hydrogenated vegetable, each as further described herein, wherein in accordance with the various embodiments, the emollient blend, the surfactant, and the hydrogenated vegetable oil are present at a ratio of from about 2:2:1 to about 4:4:1, by weight, based on the weight of the composition. Thus, in some embodiments, the emollient blend, the surfactant, and the hydrogenated vegetable oil are present at a ratio of about 2:2:1 by weight, based on the weight of the composition. In other embodiments, the emollient blend, the surfactant, and the hydrogenated vegetable oil are present, by weight, at a ratio of about 3:3:1, and in yet other embodiments the emollient blend, the surfactant, and the hydrogenated vegetable oil are present at a ratio of about 4:4:1, by weight, based on the weight of the composition.

Fatty Compounds

In accordance with the disclosure, a plurality of fatty compounds is present in the composition, the plurality of fatty compounds including hydrogenated vegetable oil, and one or more additional oils selected from fatty plant derived oil and synthetic oil that comprises one or more fatty chain having a chain length from and including C8 to C24. In accordance with some embodiments, the fatty compounds are selected from one or more of castor oil, hydrogenated castor oil, and synthetic oil. In accordance with some embodiments, the fatty compounds are selected from one or more of *Ricinus communis* (castor) seed oil, *Prunus amygdalus* dulcis (sweet almond) oil, *Prunus armeniaca* (apricot) kernel oil, and *Helianthus annuus* (sunflower) seed oil.

In an particular embodiment, one or more additional oils comprising the plurality of fatty compounds includes *Ricinus communis* (castor) seed oil, *Prunus amygdalus* dulcis (sweet almond) oil, *Prunus armeniaca* (apricot) kernel oil, *Helianthus annuus* (sunflower) seed oil.

In accordance with some embodiments, one or more additional oils comprising the plurality of fatty compounds includes more than two fatty compounds.

In accordance with the various embodiments, the one or more additional oils is present in the composition at a concentration, by weight, of from about 1% to about 95%, or from about 50% to about 95%, or from about 70% to about 90%, or from about 70% to about 80%, or any suitable combination, sub-combination, range, or sub-range thereof by weight, based on the weight of the composition.

In accordance with some embodiments, the one or more additional oils is present in the composition at a concentration, by weight, of at least about 10%, based on the total weight of the protective barrier composition. In some embodiments, the one or more additional oils is present in the range from about 10% to about 50%, or from about 10% to about 30%, or from about 15% to about 30%, or from about 15% to about 25%, or any suitable combination, sub-combination, range, or sub-range thereof by weight, based on the weight of the composition.

Thus, in some embodiments, the one or more additional oils is present, by weight, based on the total weight of the composition, from about at least 10, 11, 12, 13, 14, 15, 16, 17, 18, 19, 20, 21, 22, 23 24, 25, 26, 27, 28, 29, 30, 31, 32, 22, 34 35 36, 37, 38, 39, 40, 41, 42, 43, 44, 45, 46, 47, 48, 49 to about 50 weight percent, including increments and ranges therein and there between.

In accordance with the various embodiments, each one of the hydrogenated vegetable oil and each of the one or more additional oils is present in the composition at a concentration, by weight, based on the total weight of the protective barrier composition, in the range from about 0.1% to about 50%, or from about 0.5% to about 50%, or from about 1% to about 20%, or from about 2% to about 20%, or from about 1.5% to about 15%, or from about 1.5% to about 10%, or from about 1.5% to about 5%, or from about 1.5% to about 2.5%, or from about 2.5% to about 5%, or from about 4% to about 10%, or any suitable combination, sub-combination, range, or sub-range thereof by weight, based on the weight of the composition.

Thus, each one of the hydrogenated vegetable oil and each of the one or more additional oils is present, by weight, based on the total weight of the composition, each one or the combination present from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 22, 34 35 36, 37, 38, 39, 40, 41, 42, 43, 44, 45, 46, 47, 48, 49 to about 50 weight percent, including increments and ranges therein and there between.

Triglycerides

In accordance with the disclosure, one or more triglyceride is present in the composition. Triglycerides can include caprylic/capric triglyceride, triglycerides having a chain length from and including C10 to C18, and combinations thereof. Examples of C10 to C18 triglycerides include, for example, C10 triglyceride, C11 triglyceride, etc.

In a particular embodiment, the one or more triglyceride includes caprylic/capric triglyceride together with one or more triglycerides having a chain length from and including C10 to C18.

In accordance with the various embodiments, the one or more triglycerides is present in the composition at a concentration, by weight, of between about 2% to about 50%, based on the total weight of the protective barrier composition. In accordance with the various embodiments, the one or more triglycerides is present in the composition at a concentration, by weight, of from about 2% to about 50%, or from about 2% to about 40%, or from about 10% to about 40%, or from about 20% to about 35%, or from about 22% to about 35%, or from about 25% to about 35%, or from about 25% to about 45%, or from about 30% to about 45%, or any suitable combination, sub-combination, range, or sub-range thereof by weight, based on the weight of the composition.

In some embodiments, the composition comprises a plurality of triglycerides, the combination of which is present at a concentration, by weight, of between about 20% to about 50%, based on the total weight of the protective barrier composition. In accordance with such embodiments, each one of the plurality of triglycerides is present in the composition at a concentration, by weight, based on the total weight of the protective barrier composition, in the range from about 1% to about 40%, or from about 12% to about 40%, or from about 3% to about 30%, or from about 3% to about 10%, or from about 5% to about 35%, or from about 10% to about 30%, or any suitable combination, sub-combination, range, or sub-range thereof by weight, based on the weight of the composition.

Thus, each one of or the combination of triglycerides is present, by weight, based on the total weight of the composition, each one or the combination present from about 1, 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 22, 34 35 36, 37, 38, 39, 40, 41, 42, 43, 44, 45, 46, 47, 48, 49 to about 50 weight percent, including increments and ranges therein and there between.

In accordance with some embodiments, the hydrogenated vegetable oil, the one or more additional oils selected from fatty plant derived oils and synthetic oils, and the one or more triglycerides, in combination, are present in the composition at a concentration, by weight, in the range from about 50% to about 80%, based on the total weight of the protective barrier composition. Thus, the combined amount of the hydrogenated vegetable oil, the one or more additional oils selected from fatty plant derived oils and synthetic oils, and the one or more triglycerides is present from about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, to about 80 weight percent, including increments and ranges therein and there between.

Surfactant

In accordance with the disclosure, the composition includes one or more surfactant comprising glyceryl stearate. In some embodiments, the one or more surfactant may further comprise potassium stearate and/or sodium stearate. The composition may include other stearate based surfactant compounds.

As used herein, glyceryl stearate is used to refer to the compound that is alternately identified in the art as octadecanoic acid, ester with 1,2,3 propanetriol; self-emulsifying glyceryl monostearate; and stearine.

In accordance with the various embodiments, the one or more surfactant comprising glyceryl stearate is present in the composition at a concentration ranging from about 0.01% to about 20%, by weight relative to the weight of the composition, or from about 2% to about 20%, or from about 0.1% to about 15%, or from about 0.1% to about 5% by weight, or from about 0.15% to about 4% by weight, or from about 0.5% to about 3.5%, or from about 0.75 to about 1.25%, or any suitable combination, sub-combination, range, or sub-range thereof by weight, based on the weight of the composition. In some embodiments, the one or more surfactant comprising glyceryl stearate is present from at least 0.01%, or from at least 2%. In some embodiments, one or more additional surfactants can be present in the composition according to the disclosure.

Thus, the one or more surfactant comprising glyceryl stearate is present, alone or in combination with another surfactant, by weight, based on the total weight of the composition, each one or the combination present from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Wax

In accordance with the disclosure, optionally one or more wax selected from natural and synthetic waxes is present in the composition.

Natural waxes can include animal tallow, bayberry wax, beeswax, grapefruit wax, orange peel wax, palm wax, rice bran wax, sumac wax, sunflower wax, soy wax, and combinations thereof.

In an particular embodiment, the composition comprises beeswax.

In accordance with the various embodiments, the one or wax is present in the composition at a concentration, by weight, of between about 1% to about 20%, based on the total weight of the protective barrier composition. In accordance with the various embodiments, the one or more wax is present in the composition at a concentration, by weight, of from about 1% to about 20%, or from about 1% to about 15%, or from about 1% to about 10%, or from about 1% to about 5%, or from about 1% to about 2%, or any suitable combination, sub-combination, range, or sub-range thereof by weight, based on the weight of the composition.

In some embodiments, the composition comprises a more than one wax, each one present in the composition at a concentration, by weight, based on the total weight of the protective barrier composition, in the range from about 0.5% to about 20%, or any suitable combination, sub-combination, range, or sub-range thereof by weight, based on the weight of the composition.

Thus, each one of or the combination of is present, by weight, based on the total weight of the composition, each one or the combination present from about 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Hydrating Agent

In accordance with the disclosure, in some embodiments, one or more hydrating agents may be present in the composition. Hydrating agents may be selected from and include any one or more synthetic and natural hydrating agents. Nonlimiting examples of hydrating agents include glycerin, squalane, sucrose, triacetin, monoethylene glycol, diethylene glycol, triethylene glycol, propylene glycol, butylene glycol, dipropylene glycol, diethylene glycol, hexylene glycol, glycol ethers such as monopropylene, dipropylene and tripropylene glycol alkyl($C_1$-$C_4$)ethers, glycerol, xylitol, maltitol, sorbitol, pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some particular embodiments, the composition includes one or more hydrating agent selected from glycerin, squalane.

In accordance with the various embodiments, the amount of the one or more hydrating agents may be present in a composition in the range from about 1% to about 20%, or from about 1% to about 15%, or from about 1% to about 10%, or from about 2% to about 5%, or from about 5% to about 20%, or from about 10% to about 20%, or from about 15% to about 20%, or any suitable combination, sub-combination, range, or sub-range thereof by weight, based on the weight of the composition. In some embodiments, the one or more hydrating agents is present from at least 5%, or from at least 10%, or from at least 15%.

Thus, one or a combination of hydrating agents may be present, by weight, based on the total weight of the composition, each one or the combination present from about 1, 2, 3, 4, 5, 6, 7, 8, 9, 10, 11, 12, 13, 14, 15, 16, 17, 18, 19 to about 20 weight percent, including increments and ranges therein and there between.

Solvent

In accordance with the disclosure, one or more solvents may be present in the composition. In accordance with some embodiments, the composition includes one or more solvents comprising a glycol. Glycols may be selected from and include, by way of nonlimiting examples, glycerin, caprylyl glycol, propylene glycol, propanediol, polyethylene glycol, and other glycols, and combinations of these.

In some particular embodiments, the one or more solvents comprises one or more of propanediol, caprylyl glycol, and polypropylene glycol.

In accordance with the various embodiments, the amount of the one or more solvents that may be present in the composition ranges from about 0.1% to about 20%, or of from about 0.1% to about 15%, or from about 0.1% to about 10%, or from about 0.1% to about 5%, or from about 0.2% to about 4%, or from about 0.3% to about 3%, or any suitable combination, sub-combination, range, or sub-range thereof by weight, based on the weight of the composition.

Thus, one or a combination of solvents may be present, by weight, based on the total weight of the composition, each one or the combination present from about 0.10, 0.20, 0.30, 0.40, 0.50, 0.60, 0.70, 0.80, 0.90, 1, 2, 3, 4, 5, 6, 7, 8, 9, 10, 11, 12, 13, 14, 15, 16, 17, 18, 19 to about 20 weight percent, including increments and ranges therein and there between.

Water

In accordance with the various embodiments, the compositions are essentially anhydrous or are devoid of water.

Chelating Agents

In accordance with the disclosure, in some embodiments, one or more other components comprising chelating agents can be present in the composition according to the disclosure. In some particular embodiments, chelating agents are selected from sodium phytate, ethylenediaminetetraacetic acid (EDTA), tetrasodium etidronate, tetrasodium pyrophosphate, pentasodium ethylenediamine tetramethylene phosphonate, sodium staminate and combinations of these.

In some particular embodiments, chelating agents comprise sodium phytate.

In accordance with the various embodiments, the amount of chelating agents present in the composition can be present in the composition according to the disclosure in a range from about 0.01% to about 5% by weight, or from about 0.05% to about 2% by weight, or from about 0.10% to about 1%, or from about 0.15% to about 0.5%, and from about 0.15% to about 0.2%, or any suitable combination, sub-combination, range, or sub-range thereof by weight, based on the weight of the composition.

Thus, one or a combination of chelating agents may be present, by weight, based on the total weight, each one or the combination present from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2.0, 3.0, 4.0 up to about 5.0 weight percent, including increments and ranges therein and there between.

Actives

In accordance with the disclosure, in some embodiments, there may be one or more actives present in the cosmetic composition. In some embodiments, actives used according to the disclosure may be selected from; anti-microbial components, including, but not limited to, caproyloyl glycine and sodium salicylate; antioxidants, including, but not limited to, phenolic compounds, such as chalcones, flavones, flavanones, flavanols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, phenolic terpenes, resveratrol, curcumin, pinoresinol, ferulic acid, hydroxytyrosol, cinnamic acid, caffeic acid, p-coumaric acid, baicalin, pine bark extract, ellagic acid; and vitamins and vitamin derivatives, such as panthenol, tocopherol, ascorbic acid; conditioning agents such as the silicone oil dimethicone, allantoin and dicaprylyl carbonate; clays such as kaolin; and combinations thereof. Although the aforementioned optional active components are given as an example, it will be appreciated that other optional components compatible with cosmetic applications known in the art may be used.

In some particular embodiments, actives are selected from a one or a combination of caproyloyl glycine, panthenol, and tocopherol; dimethicone, allantoin, dicaprylyl carbonate, and kaolin.

In accordance with the various embodiments, the amount of one or more actives, alone or in combination, present in the composition can be present in the composition according to the disclosure in a range from about 0.01% to about 20%, by weight, or from about 0.05% to about 15%, or from about 0.1% to about 10%, or from about 0.15% to about 5%, or from about 0.40% to about 4%, or from about 0.50% to about 2% by weight, or from about 1% to about 2%, or any suitable combination, sub-combination, range, or sub-range thereof by weight, based on the weight of the composition.

Thus, one or a combination of actives may be present, by weight, based on the total weight of the composition, each one or the combination present from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Raw Materials

Compositions as described in the representative embodiments according to the disclosure, and compositions as exemplified herein include raw materials selected from commercially available materials, including, for example: Glyceryl Dibehenate & Tribehenin & Glyceryl Behenate blend; Glyceryl Stearate; Hydrogenated Castor Oil; Glyceryl Dibehenate—all RM 100% unless otherwise noted.

EXAMPLES

Inventive Compositions

| RAW MATERIAL | INV 1 | INV 2 | INV 3 | INV 4 |
|---|---|---|---|---|
| GLYCERYL DIBEHENATE (and) TRIBEHENIN (and) GLYCERYL BEHENATE | 3.5 | 3.5 | 3.5 | 3.5 |
| GLYCERYL STEARATE | 3.5 | 3.5 | 3.5 | 3.5 |
| HYDROGENATED VEGETABLE OIL | 1.75 | 1.75 | 1.75 | 1.75 |
| RICINUS COMMUNIS (CASTOR) SEED OIL | 10 | 10 | 10 | |
| CAPRYLIC/CAPRIC TRIGLYCERIDE | 27.05 | 32.05 | 32.55 | 27.55 |
| C10-18 TRIGLYCERIDES | 10 | 3 | 10 | 10 |
| HELIANTHUS ANNUUS (SUNFLOWER) SEED OIL | 15 | 16 | 15 | 15 |
| PRUNUS AMYGDALUS DULCIS (SWEET ALMOND) OIL | 4 | 5 | 4 | 4 |
| OLEA EUROPAEA (OLIVE) FRUIT OIL | | | | 10 |
| ISOPROPYL MYRISTATE | | | | 5 |
| HYDROGENATED POLYISOBUTENE | 5 | 5 | | |
| CAPRYLOYL GLYCINE | 0.4 | 0.4 | 0.4 | 0.4 |
| GLYCERIN | 15 | 15 | 15 | 15 |
| CAPRYLYL GLYCOL | 0.3 | 0.3 | 0.3 | 0.3 |
| PROPANEDIOL | 3 | 3 | 3 | 3 |
| ACTIVES | 1.5 | 1.5 | 1 | 1 |

| RAW MATERIAL | INV 5 | INV 6 | INV 7 | INV 8 |
|---|---|---|---|---|
| GLYCERYL DIBEHENATE (and) TRIBEHENIN (and) GLYCERYL BEHENATE | 3.5 | 4 | 4 | 4 |
| GLYCERYL STEARATE | 3.5 | 4 | 4 | 4 |
| HYDROGENATED VEGETABLE OIL | 1 | 1.25 | 1.25 | 1.25 |
| CAPRYLIC/CAPRIC TRIGLYCERIDE | 29.1 | 27.6 | 22.6 | 23 |
| C10-18 TRIGLYCERIDES | 10 | 10 | 10 | 10 |
| HELIANTHUS ANNUUS (SUNFLOWER) SEED OIL | 15 | 20 | 20 | 20 |
| PRUNUS AMYGDALUS DULCIS (SWEET ALMOND) OIL | 4 | 2.5 | 2.5 | 2.5 |
| PRUNUS ARMENIACA (APRICOT) KERNEL OIL | 10 | 7 | 7 | 7 |
| DICAPRYLYL CARBONATE | 3 | 3 | 3 | 3 |
| BEESWAX | 1.5 | 2 | 2 | 2 |
| CAPRYLOYL GLYCINE | 0.4 | 0.4 | 0.4 | |
| GLYCERIN | 15 | 15 | 20 | 20 |
| PROPANEDIOL | 3 | 3 | 3 | 3 |
| ACTIVES | 1 | 0.25 | 0.25 | 0.25 |

Comparative Compositions

Aquaphor:

Active ingredient: Petrolatum (41%); Inactive ingredients: Mineral Oil, Ceresin, Lanolin Alcohol, Panthenol, Glycerin, Bisabolol.

Aqua Baume: silicone and water emulsion

Inventive and Comparative Testing:

Transepidermal Water Loss (TEWL) was determined in a bench system (simulating live skin) to evaluate skin barrier performance of a representative inventive composition in comparison to a commercial mineral oil-based composition, and the standard silicone and water emulsion. The inventive composition INV 8 listed above was prepared according to the above described method. TEWL testing included use of an automated system which measures water loss from a chamber through a treated membrane over an extended period of time with controlled temperature and humidity. According to the method, fixed volumes of water were deposited in each chamber and fixed amounts of each tested composition applied to the membrane of each respective test chamber. The lower the TEWL water loss flux value, the less water loss would be expected through the skin, and thus the greater occlusive barrier protection.

Test results are shown in FIG. 1. The data represent the average of three trials with each composition. As expected, the greatest water loss was observed with the Aqua Baume control (~265 g m$^{-2}$ h$^{-1}$) which lacks any occlusive components. As shown, the inventive composition demonstrated reduced water loss as compared with the Aqua Baume control, and performed comparably to the mineral oil-based Aquaphor composition (~180 g m$^{-2}$ h$^{-1}$ for INV 8 vs. 150 g m$^{-2}$ h$^{-1}$ for Aquaphor). The data clearly show that the inventive composition that comprises the emollient composition, surfactant and oil according to the disclosure provides an occlusive barrier that is surprisingly comparable to that provided by a conventional mineral-oil based composition.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"One or more," as used herein, means at least one, and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A protective barrier composition, consisting of:
   (i) an emollient blend comprising glyceryl dibehenate, tribehenin, and glyceryl behenate with or without a solvent;
   (ii) glyceryl stearate;
   (iii) hydrogenated vegetable oil;
   (iv) one or more additional oils selected from the group consisting of fatty plant derived oils, synthetic oils, and a combination thereof, the fatty plant derived oils and synthetic oils having one or more fatty chains having a chain length from and including C8 to C24;
   (v) one or more triglycerides present in the composition at a concentration, by weight, in the range from about 2% to about 50%, based on the total weight of the protective barrier composition;
   (vi) one or more ingredients selected from the group consisting of waxes, hydrating agents, solvents, antimicrobials, antioxidants, actives, vitamins, vitamin derivatives, and combinations thereof;
   wherein the emollient blend, the glyceryl stearate, and the hydrogenated vegetable oil are present, by weight, at a ratio of from about 2:2:1 to about 4:4:1, based on the weight of the protective barrier composition; and
   wherein the protective barrier composition provides an occlusive barrier to keratinous tissue.

2. The protective barrier composition of claim 1, wherein the emollient blend, the glyceryl stearate, and the hydrogenated vegetable oil are present, by weight, at a ratio of about 2:2:1.

3. The protective barrier composition of claim 1, wherein the emollient blend, the glyceryl stearate, and the hydrogenated vegetable oil are present, by weight, at a ratio of about 3:3:1.

4. The protective barrier composition of claim 1, wherein the emollient blend, the glyceryl stearate, and the hydrogenated vegetable oil are present, by weight, at a ratio of about 4:4:1.

5. The protective barrier composition of claim 1, wherein the glyceryl dibehenate, tribehenin and glyceryl behenate of the emollient blend are present, by weight, at a ratio of about 1:1:1, based on the weight of the emollient blend.

6. The protective barrier composition of claim 1, wherein each of the emollient blend and the glyceryl stearate is present in the composition at a concentration, by weight, of at least about 2% and up to about 20%, based on the total weight of the protective barrier composition.

7. The protective barrier composition of claim 1, wherein the hydrogenated vegetable oil is present in the composition at a concentration, by weight, in the range from about 0.1% to about 20%, based on the total weight of the protective barrier composition.

8. The protective barrier composition of claim 1, wherein the composition includes wax present in the composition at a concentration, by weight, in the range from about 0% to about 20%, based on the total weight of the protective barrier composition.

9. The protective barrier composition of claim 1, wherein the composition includes wax present in the composition at a concentration, by weight, in the range from about 1% to about 20%, based on the total weight of the protective barrier composition.

10. The protective barrier composition of claim 1, wherein the one or more additional oils selected from the group consisting of one or more fatty plant derived oils, synthetic oils, and a combination thereof are present in the composition at a concentration, by weight, of from about 10% to about 50%, based on the total weight of the protective barrier composition.

11. The protective barrier composition of claim 10, wherein the one or more additional oils selected from the group consisting of one or more fatty plant derived oils, synthetic oils, and a combination thereof are present in the composition at a concentration, by weight, of from about 25% to about 35%, based on the total weight of the protective barrier composition.

12. The protective barrier composition of claim 1, wherein the one or more additional oils selected from the group consisting of one or more fatty plant derived oils, synthetic oils, and a combination thereof includes one or more of *Prunus amygdalus* dulcis oil, *Olea europaea* fruit oil, or *Helianthus annuus* seed oil.

13. The protective barrier composition of claim 1, wherein the one or more additional oils selected from the group consisting of one or more fatty plant derived oils, synthetic oils, and a combination thereof includes a synthetic hydrogenated oil present in the composition at a concentration, by weight, of from about 1% to about 10%, based on the total weight of the protective barrier composition.

14. The protective barrier composition of claim 1, wherein the one or more triglycerides is selected from the group consisting of caprylic/capric triglyceride, triglycerides having a chain length from and including C10 to C18, and combinations thereof.

15. The protective barrier composition of claim 1, wherein the hydrogenated vegetable oil, the one or more additional oils selected from the group consisting of one or more fatty plant derived oils, synthetic oils, and a combination thereof, and the one or more triglycerides, in combination, are present in the composition at a concentration, by weight, in the range from about 50% to about 80%, based on the total weight of the protective barrier composition.

16. The protective barrier composition of claim 1, wherein the composition includes one or more hydrating agents present in the composition at a concentration, by weight, in the range from about 10% to about 20%, based on the total weight of the protective barrier composition.

17. The protective barrier composition of claim 1, wherein the composition includes one or more hydrating agents selected from the group consisting of glycerin and squalane, and combinations thereof.

18. The protective barrier composition of claim 1, wherein the composition includes one or more solvents present in the composition at a concentration, by weight, in the range from about 1% to about 20%, based on the total weight of the protective barrier composition.

19. The protective barrier composition of claim 1, wherein the composition includes one or more solvents selected from glycols.

20. The protective barrier composition of claim 19, wherein the one or more solvents is selected from the group consisting of propanediol, caprylyl glycol, polypropylene glycol, and combinations thereof.

21. The protective barrier composition of claim 1, wherein the one or more ingredients selected from the group consisting of waxes, hydrating agents, solvents, antimicrobials, antioxidants, actives, vitamins, vitamin derivatives, and combinations thereof includes one or more ingredients selected from the group consisting of actives, vitamins, vitamin derivatives, and combinations thereof.

22. The protective barrier composition of claim 21, wherein the composition includes one or more ingredients selected from the group consisting of capryloyl glycine, tocopherol, panthenol, sodium phytate, dimethicone, allantoin, dicaprylyl carbonate, kaolin, and combinations thereof.

23. The protective barrier composition of claim 1, wherein the protective barrier composition is essentially free of one or more of petrolatum, mineral oil and lanolin.

24. The protective barrier composition of claim 1, wherein the composition is essentially anhydrous.

25. A protective barrier composition, consisting of:
(i) an emollient blend comprising glyceryl dibehenate, tribehenin and glyceryl behenate with or without a solvent;
(ii) glyceryl stearate;
wherein each of the emollient blend and the glyceryl stearate is present in the composition at a concentration, by weight, in the range from about 2% to about 20%, based on the total weight of the protective barrier composition, and wherein the combination of the emollient blend and the glyceryl stearate is present in the composition at a concentration, by weight, of up to and including about 30%, based on the total weight of the protective barrier composition; and
(iii) hydrogenated vegetable oil present in the composition at a concentration, by weight, in the range from about 0.1% to about 20%;
(iv) one or more additional oils selected from the group consisting of fatty plant derived oils, synthetic oils, and a combination thereof, the one or more additional oils present in the composition at a concentration, by weight, of from about 10% to about 50%, based on the total weight of the protective barrier composition;
(v) one or more triglycerides present in the composition at a concentration, by weight, in the range from about 20% to about 50%, based on the total weight of the protective barrier composition; and
(vi) one or more ingredients selected from the group consisting of waxes, hydrating agents, solvents, antimicrobials, antioxidants, actives, vitamins, vitamin derivatives, and combinations thereof;
wherein the protective barrier composition provides an occlusive barrier to keratinous tissue.

26. The protective barrier composition of claim 25, wherein the composition includes a hydrating agent present in the composition at a concentration, by weight, in the range from about 10% to about 20%, based on the total weight of the protective barrier composition.

27. The protective barrier composition of claim 25, wherein the ingredients selected from the group consisting of waxes, hydrating agents, solvents, antimicrobials, antioxidants, actives, vitamins, vitamin derivatives, and combinations thereof includes one or more ingredients selected from the group consisting of actives, vitamins, vitamin derivatives, and combinations thereof.

28. The protective barrier composition of claim 27, wherein the composition includes one or more ingredients selected from the group consisting of capryloyl glycine, tocopherol, panthenol, sodium phytate, dimethicone, allantoin, dicaprylyl carbonate, kaolin, and combinations thereof.

29. The protective barrier composition of claim 25, wherein the protective barrier composition excludes petrolatum, mineral oil and lanolin and is essentially anhydrous.

30. A protective barrier composition, consisting of:
(i) an emollient blend of glyceryl dibehenate, tribehenin and glyceryl behenate with or without a solvent;
(ii) glyceryl stearate;
wherein each of the emollient blend and the glyceryl stearate is present in the composition at a concentration, by weight, in the range from about 2% to about 20%, based on the total weight of the protective barrier composition, and wherein the combination of the emollient blend and the glyceryl stearate is present in the composition at a concentration, by weight, of up to and including about 30%, based on the total weight of the protective barrier composition;
(iii) hydrogenated vegetable oil present in the composition at a concentration, by weight, in the range from about 0.1% to about 20%;
(iv) one or more additional oils selected from one or more fatty plant derived oils and synthetic oils, the one or more additional oils present in the composition at a concentration, by weight, of from about 20% to about 50%, based on the total weight of the protective barrier composition;

(v) one or more triglycerides present in the composition at a concentration, by weight, in the range from about 20% to about 50%, based on the total weight of the protective barrier composition;
(vi) one or more waxes present in the composition at a concentration, by weight, in the range from about 1% to about 20%;
(vii) one or more hydrating agents present in the composition at a concentration, by weight, in the range from about 10% to about 20%, based on the total weight of the protective barrier composition; and
(viii) one or more ingredients selected from the group consisting of solvents, antimicrobials, antioxidants, actives, vitamins, vitamin derivatives, and combinations thereof;
wherein the protective barrier composition provides an occlusive barrier to keratinous tissue.

31. The protective barrier composition of claim 30, wherein the composition includes one or more solvents selected from the group consisting of propanediol, caprylyl glycol, polypropylene glycol, and combinations thereof.

32. The protective barrier composition of claim 30, wherein the one or more hydrating agents is selected from the group consisting of glycerin, squalane, and combinations thereof.

33. The protective barrier composition of claim 32, wherein the protective barrier composition excludes petrolatum, mineral oil and lanolin and is essentially anhydrous.

34. A protective barrier composition, consisting of:
(i) an emollient blend consisting of glyceryl dibehenate, tribehenin and glyceryl behenate with or without a solvent;
(ii) glyceryl stearate;
(iii) hydrogenated vegetable oil;
(iv) one or more additional oils selected from the group consisting of fatty plant derived oils, synthetic oils, and a combination thereof, the fatty plant derived oils and synthetic oils having one or more fatty chains having a chain length from and including C8 to C24;
(v) one or more triglycerides;
(vi) wax; and
(vii) one or more ingredients selected from the group consisting of glycerin, squalane, propanediol, caprylyl glycol, polypropylene glycol, capryloyl glycine, tocopherol, panthenol, sodium phytate, dimethicone, allantoin, dicaprylyl carbonate, kaolin, and combinations thereof;
wherein the protective barrier composition provides an occlusive barrier to keratinous tissue.

35. The protective barrier composition of claim 34, wherein the emollient blend, the glyceryl stearate, and the hydrogenated vegetable oil are present, by weight, at a ratio of from about 2:2:1 to about 4:4:1, based on the weight of the protective barrier composition.

36. The protective barrier composition of claim 34, wherein the one or more additional oils selected from the group consisting of fatty plant derived oils, synthetic oils, and a combination thereof includes one or more of *Prunus amygdalus* dulcis oil, *Olea europaea* fruit oil, or *Helianthus annuus* seed oil.

* * * * *